United States Patent [19]

O'Donnell

[11] Patent Number: 5,702,701

[45] Date of Patent: Dec. 30, 1997

[54] TREATMENT OF SOIL AND PLANTS WITH A COMPOSITION CONTAINING *BACILLUS LATEROSPORUS*

[75] Inventor: Boyd O'Donnell, San Marcos, Calif.

[73] Assignee: The O'Donnell Family Investment Trust, San Marcos, Calif.

[21] Appl. No.: 484,784

[22] Filed: Jun. 7, 1995

Related U.S. Application Data

[63] Continuation-in-part of Ser. No. 236,701, Apr. 28, 1994, Pat. No. 5,455,028, which is a continuation of Ser. No. 908,631, Jul. 1, 1992, abandoned, which is a continuation of Ser. No. 621,603, Dec. 4, 1990, abandoned.

[51] Int. Cl.$^6$ ............................................ C12N 1/20
[52] U.S. Cl. ......................... 424/93.46; 435/252.5
[58] Field of Search ..................... 424/93.46; 435/252.5

[56] References Cited

U.S. PATENT DOCUMENTS

| | | | |
|---|---|---|---|
| 4,582,704 | 4/1986 | Baker et al. | 424/93.462 |
| 4,663,162 | 5/1987 | Kado et al. | 424/93.46 |
| 4,952,229 | 8/1990 | Muir | 71/7 |
| 5,045,314 | 9/1991 | Bone et al. | 424/93.46 |
| 5,055,293 | 10/1991 | Aronson et al. | 424/93.46 |

FOREIGN PATENT DOCUMENTS 51305492  3/1976  Japan .

OTHER PUBLICATIONS

Maksimova et al., Chemical nature of nitrorespiration in microorganisms isolated from corn silage, Izv. Timiryazevsk S–kd. Akad. 4: 114–20 (1993), see the abstract.

*Journal of Phytopathology*, vol. 138, No. 3, 1993, pp. 189–208, XP 000610785, A.M. Rosales et al.: "Identification of Some Bacteria from Paddy Antagonistc to Several Rice Fungal Pathogens".

*Pesticide Science*, vol.37, No. 4, 1993, Barking Essex, G.B., pp. 355–363, XP 000385372, J.O. Becker et al., "Control of Soil–borne Pathogens with Living Bacteria and Fungi: Status and Outlook ".

*Chemical Patents Index, Basic Abstracts Journal*, Week 8730, Sep. 23, 1987, Derwent Publications Ltd., London, G.B., AN 87–210719, XP 002019403 & JP,A, 62 138 380 (Biostar K.K.).

*Chemical Patents Index, Basic Abstracts Journal*, Week 8830, Sep. 21, 1988, Derwent Publications Ltd., London, G.B., AN 88–209768, XP 002019404 & JP,A, 63 146 723 (Sankyo Yuki KK).

*Trends in Biotechnology*, vol. 7, No. 2, Feb. 1989, Cambridge, G.B., pp. 39–44, XP 002019402, J.W. Kloepper et al.: "Free–living bacterial inocula for enhancing crop productivity".

*Primary Examiner*—Jean C. Witz
*Attorney, Agent, or Firm*—Lyon & Lyon LLP

[57] ABSTRACT

A method for treating soil with a composition containing the microorganism *Bacillus laterosporus* strain BOD is disclosed. Treatment of the soil with *B. laterosporus* strain BOD results in certain beneficial changes to the soil including maintenance of an alkaline pH, fixation of plant nutrients, neutralization of odors, a reduction in aerobic and coliform bacterial counts, and inhibition of plant pathogenic bacteria and fungi. A method for treating plants with *B. laterosporus* strain BOD to inhibit the growth of plant pathogenic organisms is also disclosed.

20 Claims, No Drawings

TREATMENT OF SOIL AND PLANTS WITH A COMPOSITION CONTAINING *BACILLUS LATEROSPORUS*

RELATED APPLICATION

This application is a continuation-in-part of application Ser. No. 08/236,701 filed Apr. 28, 1994, now U.S. Pat. No. 5,455,028 which is a continuation of application Ser. No. 07/908,631 filed Jul. 1, 1992, now abandoned, which is a continuation of application Ser. No. 07/621,603 filed Dec. 4, 1990, now abandoned.

TECHNICAL FIELD

The present invention relates generally to a method for treating soil to improve the soil for agronomic purposes and for other purposes. The present invention also relates to a method of treating plants to control certain plant pathogenic organisms.

BACKGROUND ART

*Bacillus laterosporus* was not previously known for use in treating soil. A previously known method for increasing the alkalinity of the soil is to add lime. The ability to maintain an alkaline soil pH with *Bacillus laterosporus* is the equivalent to the use of tons of lime per acre per year. *Bacillus laterosporus* was not previously known for use in controlling plant pathogenic organisms.

SUMMARY OF THE INVENTION

The present invention is directed to methods for treating soil and plants, using a composition comprising the microorganism *Bacillus laterosporus* strain BOD.

In one separate aspect of the present invention, a method of treating soil with *Bacillus laterosporus* strain BOD to maintain an alkaline pH is contemplated.

In a further separate aspect of the present invention, a method of treating soil with *Bacillus laterosporus* strain BOD to reduce the aerobic bacterial count is contemplated.

In a further separate aspect of the present invention, a method of treating soil with *Bacillus laterosporus* strain BOD to reduce soil odor is contemplated.

In a further separate aspect of the present invention, a method of treating soil with *Bacillus laterosporus* strain BOD to inhibit plant pathogenic organisms is contemplated.

In a further separate aspect of the present invention, a method of treating plants with *Bacillus laterosporus* strain BOD to inhibit plant pathogenic organisms is contemplated.

Accordingly, an object of the present invention is to provide methods for treating soil and plants with *Bacillus laterosporus* strain BOD.

DETAILED DESCRIPTION OF THE INVENTION

Treatment of soil with a composition containing *B. laterosporus* strain BOD results in a number of beneficial changes for agronomic purposes. The *B. laterosporus* strain BOD that are added to the soil maintain the pH level of the soil in the alkaline range. The ability to perform this function is equal to tons of lime per acre per year. The maintenance of the soil in the alkaline range has a number of advantages. These include fixing soil nutrients by preventing the acidification of the soil and the resulting leaching of nutrients. Ammonia nitrogen which is easily lost into the air is converted in alkaline pH soil to nitrate nitrogen which is fixed in the soil and easily assimilated by plants. Potassium is more insoluble at high pH and therefore less likely to be leached out by rain. The *B. laterosporus* strain BOD was also effective in eliminating odors. This anti-odor effect was probably due, at least partially, to the maintenance of a more alkaline pH.

The *B. laterosporus* strain BOD composition is also effective in altering the microbial composition of the soil. These alterations include decreasing the overall number of aerobic bacteria. The reduction in bacteria include a reduction in Salmonella species, Klebsiella species, *Escherichia coli*, Staphylococcus species and total coliform species. The reduction of these bacterial populations indicates a reduction in potentially pathogenic microorganisms. The probable mechanism by which these changes occur is through the maintenance of an alkaline pH, which inhibits the growth of acid bacteria. Other possible factors are the production of metabolites by the *B. laterosporus* which interfere with coliform growth or the competition between *B. laterosporus* strain BOD and the pathogenic bacteria.

*B. laterosporus* strain BOD was originally isolated from a soil sample from Iceland and was selected for further research based on its ability to inhibit pathogenic bacteria in soil and lab test media. The examples described herein utilize *B. laterosporus* strain BOD to treat soil. Table I below shows the results obtained when soil was treated with *B. laterosporus* strain BOD. Treated soil and untreated soil were compared 30 days after treatment.

TABLE I

| ANALYSIS | CONTROL | 30 DAYS | % CHANGE |
|---|---|---|---|
| aerobic bacteria plate count | $52 \times 10^6$/gm | $30 \times 10^6$/gm | −42% |
| total coliform bacteria | 460/gm | 23/gm | −95% |
| E. coli (fecal coliform) | 460/gm | <3/gm | −99% |
| coagulate positive Staph. | 23/gm | <3/gm | −87% |
| Salmonella detection | pos./25 gm | neg./25 gm | −99% |
| Klebsiella detection | pos./25 gm | neg./25 gm | −99% |
| hydrogen ion (pH) | 7.75 pH | 8.45 pH | +9% |
| total kjeldahl nitrogen | 1,095 ppm | 1,235 ppm | +13% |
| potassium | 7,372 ppm | 8,319 ppm | +13% |
| phosphorous | 510 ppm | 524 ppm | +3% |

In another experiment in the laboratory, *B. laterosporus* strain BOD was shown to be effective in inhibiting the growth of certain plant pathogenic bacteria and fungi in culture. The bacteria include *Clavibacter michiganense, Erwinia carotovora, Erwinia chrysanthemi, Pseudomonas solanacearum, Pseudomonas syringae,* and *Xanthomonas campestris*. The fungi include Aspergillus species, Bipolaris species, Cephalosporium species, Chaetomium species, *Colletotrichum magna, Fusarium oxysporum,* Penicillium species, *Phytophthora cinnamomi, Phytophthora citricola, Phytophthora citrophthora, Phytophthora parasitica, Pythium aphanidermatum, Pythium ultimum, Rhizoctonia solani, Sclerotium rolfsii, Verticillium albo-atrum, Verticillium dahliae,* and Verticillium species. Because *B. laterosporus* strain BOD was shown to be effective in the laboratory for inhibiting the growth of the above described species, it is expected that the application of *B. laterosporus* strain BOD to the soil will be effective as a soil treatment to inhibit certain plant pathogenic organisms, including bacteria and fungi, and thereby reduce or eliminate certain plant diseases. Additionally, it is expected that the application of *B. laterosporus* strain BOD directly to plants will be an effective means for controlling certain plant pathogenic bacteria and fungi.

APPLICATION

*B. laterosporus* strain BOD can be mixed with water and applied to the soil in the normal course of irrigation, including spray irrigation, drip irrigation, or any other means of irrigation. Alternatively, it can be applied independently of irrigation, i.e soil injection, topical application. Effective ranges for application are between about $3.785 \times 10^9$ cells per acre and $3.785 \times 10^{12}$ cells per acre. The most effective range would be expected to be between about $3 \times 10^{10}$ cells per acre and $2 \times 10^{11}$ cells per acre. Generally, a relatively high initial application will be followed by periodic applications thereafter, for as long as necessary to maintain the desired effects. The bacteria could also be applied to the soil as a mixture with other soil additives such as fertilizers, herbicides, or pesticides. The bacteria could also be applied in a dry form such as in a powder, either alone or in formulation with other inert or active ingredients.

BEST MODE FOR CARRYING OUT THE INVENTION

The preferred method and composition for treating soil with *B. laterosporus* strain BOD consists of using *B. laterosporus* strain BOD at a concentration of 10 million cells per milliliter of water. The water/bacteria mixture is applied to the soil by irrigation spraying at an initial rate of two gallons per acre and then applied periodically at a rate of one gallon per acre. Therefore, the initial application is with $7.57 \times 10^{10}$ cells per acre, and the periodic application thereafter is with $3.785 \times 10^{10}$ cells per acre. The soil is treated periodically for as long as necessary to maintain the desired effects.

*Bacillus laterosporus* strain BOD was deposited at the American Type Culture Collection (ATCC) in Rockville, Md. on Nov. 12, 1990 and assigned Accession Number ATCC 55122. The present invention is not to be limited in scope by the organism deposited, since the deposited organism is intended to serve only as an example of one strain of *B. laterosporus* that would be effective in carrying out the invention. The term "*Bacillus laterosporus* strain BOD", for the purposes of this invention, is intended to mean any strain of *Bacillus laterosporus* that is effective in treating soil and plants as described herein.

Variations on the specific illustrations of the invention disclosed herein will be apparent to those skilled in the art, and it is intended that this invention be limited only by the scope of the appended claims.

What is claimed is:

1. A method for improving the quality of soil for agronomic purposes, comprising the step of applying to the soil an effective amount of a composition comprising *Bacillus laterosporus* strain BOD having all of the identifying characteristics of ATCC Accession Number 55122.

2. A method according to claim 1 wherein the *Bacillus laterosporus* strain BOD is applied to the soil in an amount of between about $3 \times 10^{10}$ cells per acre and $2 \times 10^{10}$ cells per acre.

3. A method according to claim 1 wherein the method results in an increase in soil pH.

4. A method according to claim 1 wherein the method results in a soil pH of between about 7.5 and 8.5.

5. A method according to claim 1 wherein the method results in a soil pH of between about 8.0 and 8.25.

6. A method according to claim 1 wherein the method results in a reduction of soil odor.

7. A method according to claim 1 wherein the method results in a reduced count of aerobic bacteria.

8. A method according to claim 1 wherein the method results in a reduced count of coliform bacteria.

9. A method according to claim 1 wherein the method results in control of plant pathogenic bacteria.

10. A method according to claim 1 wherein the method results in control of plant pathogenic fungi.

11. A method of treating plants to inhibit the growth of plant pathogenic organisms, comprising the step of administering to the plants an effective amount of a composition comprising *Bacillus laterosporus* strain BOD having all of the identifying characteristics of ATCC Accession Number 55122.

12. A method according to claim 11 wherein the plant pathogenic organism is a bacteria.

13. A method according to claim 11 wherein the plant pathogenic organism is a fungi.

14. A method according to claim 1 wherein the *Bacillus laterosporus* strain BOD is applied to the soil in an amount between $3.785 \times 10^9$ cells per acre and $3.785 \times 10^{12}$ cells per acre.

15. A method according to claim 1 wherein the *Bacillus laterosporus* strain BOD is mixed with a soil additive selected from the group consisting of fertilizer, herbicide and pesticide.

16. A method according to claim 1 wherein the composition is mixed with water and applied to the soil in the normal course of irrigation.

17. A method according to claim 1 wherein $7.57 \times 10^{10}$ *Bacillus laterosporus* strain BOD cells per acre are initially applied to the soil followed by periodic application of $3.785 \times 10^{10}$ *Bacillus laterosporus* strain BOD cells per acre.

18. A method of altering the microbial composition of soil, comprising the step of applying to the soil an effective amount of *Bacillus laterosporus* strain BOD having all of the identifying characteristics of ATT Accession Number 55122.

19. A method according to claim 18 wherein the method results in a reduced count of a species of bacteria selected from the group consisting of Salmonella, Klebsiella, *Escherichia coil* and Staphylococcus.

20. A method according to claim 18 wherein about $3.785 \times 10^9$ to $3.785 \times 10^{12}$ *Bacillus laterosporus* strain BOD cells per acre are applied to the soil.

* * * * *

UNITED STATES PATENT AND TRADEMARK OFFICE
CERTIFICATE OF CORRECTION

PATENT NO. : 5,702,701
DATED : December 30, 1997
INVENTOR(S) : O'Donnell, Boyd

It is certified that error appears in the above-indentified patent and that said Letters Patent is hereby corrected as shown below:

Column 4, line 54, change "Escherichia coil" to --Escherichia coli--.

Signed and Sealed this

Sixth Day of October, 1998

Attest:

BRUCE LEHMAN

Attesting Officer     Commissioner of Patents and Trademarks